US008298488B1

(12) United States Patent
Lewis et al.

(10) Patent No.: US 8,298,488 B1
(45) Date of Patent: Oct. 30, 2012

(54) MICROFABRICATED THERMIONIC DETECTOR

(75) Inventors: Patrick R. Lewis, Albuquerque, NM (US); Ronald P. Manginell, Albuquerque, NM (US); David R. Wheeler, Albuquerque, NM (US); Daniel E. Trudell, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 1677 days.

(21) Appl. No.: 10/981,010

(22) Filed: Nov. 4, 2004

(51) Int. Cl.
*G01N 27/00* (2006.01)
(52) U.S. Cl. .............. 422/98; 422/82.01; 422/82.02; 422/82.03; 422/83; 422/88; 422/89; 422/90; 422/94; 422/95; 422/96; 422/97; 436/149; 436/150; 436/151; 436/152; 436/153
(58) Field of Classification Search .............. 436/153, 436/149, 150, 151, 152; 422/83, 89, 90, 422/98, 93, 82.01, 82.02, 82.03, 88, 94, 95, 422/96, 97
See application file for complete search history.

(56) References Cited

U.S. PATENT DOCUMENTS

| | | | | |
|---|---|---|---|---|
| 3,423,181 | A * | 1/1969 | Trone Elmer et al. | 422/54 |
| 4,524,047 | A * | 6/1985 | Patterson | 422/98 |
| 5,345,213 | A * | 9/1994 | Semancik et al. | 338/34 |
| 5,386,115 | A * | 1/1995 | Freidhoff et al. | 250/281 |
| 5,493,177 | A * | 2/1996 | Muller et al. | 313/578 |
| 5,498,548 | A * | 3/1996 | White et al. | 436/149 |
| 5,747,815 | A * | 5/1998 | Young et al. | 250/423 R |
| 6,527,835 | B1 * | 3/2003 | Manginell et al. | 96/102 |
| 6,786,716 | B1 * | 9/2004 | Gardner et al. | 431/268 |
| 2003/0052263 | A1 * | 3/2003 | Kaufman et al. | 250/281 |

OTHER PUBLICATIONS

Fujii et al, Thermionic Ionization Detector with Lanthanum Hexaboride/Silicon Dioxide Thermionic Emitter Material for Gas Chromatography, Anal. Chem. 1985, 57, 490-493.*
Robert Manley, "Design and Fabrication of a Micro-Size Thermionic Ionization/Flame Ionization Detector for Gas Phase Chemical Analytes", May 11, 2004, 22nd Annual Microelectronic Engineering Conference. Powerpoint Slides 1-18.*
Robert Manley, "Design and Fabrication of a Micro-Size Thermionic Ionization/Flame Ionization Detector for Gas Phase Chemical Analytes", May 11, 2004, 22nd Annual Microelectronic Engineering Conference. p. 80-84.*
Perng et al, "Micromachined Thermionic Emitters", 1992, J. Micromech. Microeng., vol. 2, No. 1, pp. 25-30.*
U.S. Appl. No. 10/903,329, filed Jul. 29, 2004, Manginell, et al.
Greg Frye-Mason, Hand-Held Miniature Chemical Analysis System (μChemLab) for Detection of Trace Concentrations of Gas Phase Analytes, Proc, Micro Total Analysis Systems, 2000, SAND2000-1480A.
Manginell, Selective, Pulsed CVD of Platinum on Microfilament Gas Sensors, Tech. Digest 1996, Solid State & Activator Workshop (1996).
Manginell, In-Situ Monitoring of Micro-Chemical Vapor Deposition (μCVD): Experimental Results and Spice Modeling, Tech. Digest 1998, Solid State & Activator Workshop, p. 371 (1998).

(Continued)

*Primary Examiner* — Dennis M White
(74) *Attorney, Agent, or Firm* — Kevin W. Bieg

(57) ABSTRACT

A microfabricated TID comprises a microhotplate and a thermionic source disposed on the microhotplate. The microfabricated TID can provide high sensitivity and selectivity to nitrogen- and phosphorous-containing compounds and other compounds containing electronegative function groups. The microfabricated TID can be microfabricated with semiconductor-based materials. The microfabricated TID can be combined with a microfabricated separation column and used in microanalytical system for the rapid on-site detection of pesticides, chemical warfare agents, explosives, pharmaceuticals, and other organic compounds that contain nitrogen or phosphorus.

17 Claims, 3 Drawing Sheets

OTHER PUBLICATIONS

Patterson, A Comparison of Different Methods of Ionizing GC Effluents, Journal of Chromatographic Science, vol. 24, Nov. 1986, p. 466-472.

Patterson, Recent Advances in Thermionic Ionization Detection for Gas Chromatography, Journal of Chromatographic Science, vol. 24, Feb. 1986, p. 41-52.

* cited by examiner

MICROFABRICATED THERMIONIC DETECTOR

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to gas chromatographic detectors and, more particularly, to a microfabricated thermionic detector for use with a microanalytical system.

BACKGROUND OF THE INVENTION

Gas chromatographic (GC) detectors are based on a variety of physical and chemical processes. Some of the most widely used GC detectors function by converting chemical species in the GC effluent to gas-phase ions, which can then be collected and directly transduced to an electrical signal. For example, the flame ionization detector (FID) is the most universally applied GC detector, because of its high sensitivity, wide dynamic range, and ability to detect a variety of organic compounds. However, the FID is a nonspecific detector that responds, in general, to all chemical compounds that contain carbon.

Particularly when the compound of interest cannot be easily resolved above background, it may be advantageous to employ a selective detector that responds only to a few limited compounds with little or no response to interfering compounds. A thermionic detector (TID), as known as a nitrogen-phosphorous detector (NPD), is such an element-specific ionization detector. The TID relies on the specific ionization of the sample compound near a hot thermionic surface, resulting from the high selectivity of surface ionization with respect to the ionization potential of the sample compound. Therefore, the TID can provide very specific ionization of sample compounds containing electronegative functional groups, such as nitrogen, phosphorous, halogen atoms, and sulfur. A conventional TID typically has a ratio of $10^4:1$ selectivity over carbon. Because of its sensitivity and selectivity for nitrogen and phosphorus, the TID is especially useful for the analysis of pesticides, chemical warfare agents, explosives, pharmaceuticals, and other organic compounds that contain nitrogen or phosphorus.

In FIG. 1 is shown a conventional TID 10 of the type used with a laboratory-based analytical system. The TID is similar to a FID, except that a rubidium- or cesium-containing bead 11 (e.g., a rubidium silicate bead) is formed on a heater coil 12 (e.g., a platinum wire). The bead 11 is electrically heated by running a current through the coil 12 to provide a thermionic source. The temperature of the thermionic source can affect the sensitivity of the detector, since the source must remain hot enough to produce a reactive chemical environment. Typically, the source is heated to between 600 and 800° C. The bead 11 is situated above a jet 13, through which passes a sample gas (e.g., containing a nitrogen or phosphorous compound) 15 that can be mixed with hydrogen 16. Make-up gas (e.g., air or oxygen) 17 can also be introduced to dilute the hydrogen mixture. Typical flow rates for a conventional TID are 2 to 6 mL/min of $H_2$ and 60 to 200 mL/min of air, dependent on the interior volume of the detector. The negative ions produced by thermochemical reactions that occur when the gases impinge on the low work function surface of the hot bead 11 are collected by a positively biased collector electrode 18 and counted with a sensitive electrometer circuit. A typical circuit can detect 0.4 pg of nitrogen and 0.1 pg for phosphorus. See R. P. W. Scott, *Chromatographic Detectors*, Marcel Dekker (1996).

Laboratory-based analytical systems can provide precise and accurate results, however, the time between sample collection in the field and the availability of results from the laboratory can often be weeks. Portable, handheld microanalytical systems, which have been termed "chemical laboratories on a chip," are being developed to enable the rapid and sensitive on-site detection of particular chemicals, including pollutants, high explosives, and chemical warfare agents. Preferably, these microanalytical systems should provide a high chemical selectivity to discriminate against potential background interferents and the ability to perform the chemical analysis on a short time scale. In addition, low electrical power consumption and reagent usage is needed for prolonged field use. See, e.g., Frye-Mason et al., "Hand-Held Miniature Chemical Analysis System (µChemLab) for Detection of Trace Concentrations of Gas Phase Analytes," *Micro Total Analysis Systems* 2000, 229 (2000).

Although conventional TIDs are now widely used in laboratory-based analytical systems, there remains a need for a microfabricated TID that can be used with microanalytical systems. Typically, the microfabricated TID can be combined with a microfabricated separation column and used in gas chromatography analysis to detect the nitrogen and/or phosphorous content in analytes eluted from the column.

SUMMARY OF THE INVENTION

The present invention is directed to a microfabricated TID, comprising a microhotplate comprising a resistive heating element; a lid disposed on a side of the microhotplate to thereby provide a detection chamber; a low work function material disposed on a surface of the microhotplate exposed to the detection chamber to provide a thermionic source; at least one gas inlet attached to the detection chamber for introduction of a sample gas thereinto; an exhaust gas outlet attached to the detection chamber for removal of decomposition products therefrom; and an ion collection electrode disposed in the detection chamber proximate the thermionic source, wherein the electrode collects charge generated by the sample gas reacting with the thermionic source when the microhotplate is heated by the resistive heating element and a voltage is applied between the thermionic source and the electrode. The low work function material can comprise an alkali- or alkaline-earth-containing material, TiN, or $LaB_6$.

Such a microfabricated TID can provide high sensitivity and selectivity to nitrogen- and phosphorous-containing compounds and other compounds containing electronegative function groups and can minimize the usage of reagents, including hydrogen. Furthermore, the microfabricated TID does not depend on the adsorption of vapor to produce a detector signal. Therefore, compared to polymer-coated microbalances that are commonly used in microanalytical systems, the response of the microfabricated TID is instantaneous.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Miniaturization of GC detectors for portable applications has been hampered by the large heat losses experienced by microsystems, due to the large surface-to-volume ratio at the microscale. However, a microcombustor, including an on-chip flame ionization detector (microFID), has recently been disclosed in U.S. Pat. No. 6,786,716 to Gardner et al., which is incorporated herein by reference. That microcombustor uses a catalyst-coated microhotplate to overcome heat losses and provide sustained combustion on the microscale. The microhotplate comprises a thin-film heater/thermal sensor patterned on a thin insulating support membrane that is suspended from its edges over a substrate frame. This microhotplate has very low heat capacity and thermal conductivity and is an ideal platform for heating thermionic source materials placed on the surface of the support membrane.

Alternative microhotplates, comprising thermally isolated low mass supports with integral heaters, can be microfabricated with semiconductor industry technologies and are suitable platforms for the microfabricated TID of the present invention. For example, a microbridge can be formed by patterning a thin filament of the resistive heater material on a silicon wafer and underetching the filament to leave a microbridge. The thermionic source material can be placed on the thermally isolated microbridge and the analytes can be flowed over the microbridge. See R. P Manginell et al., "In-Situ Monitoring of Micro-Chemical Vapor Deposition ($\mu$-CVD): Experimental Results and SPICE Modeling," *Tech. Digest* 1998 *Sol. State Sensor and Actuator Workshop*, 371 (1998) and R. P Manginell et al., "Selective, pulsed CVD of platinum on microfilament gas sensors," *Tech. Digest* 1996 *Sol. State Sensor and Actuator Workshop*, 23 (1996), both of which are incorporated by reference. Another suitable microhotplate is the heated pivot plate resonator. The pivot plate resonator is basically a small plate, or paddle, that pivots about two torsional pivot arms and thereby enables the measurement of adsorbed mass by detecting the oscillatory motion of the paddle. Thin-film heaters can be included in the fabrication of the paddle to provide a low heat capacity, thermally stable platform on which the thermionic source material can be placed. See U.S. patent application Ser. No. 10/903,329 to Manginell et al., which is incorporated herein by reference.

Figure 1:
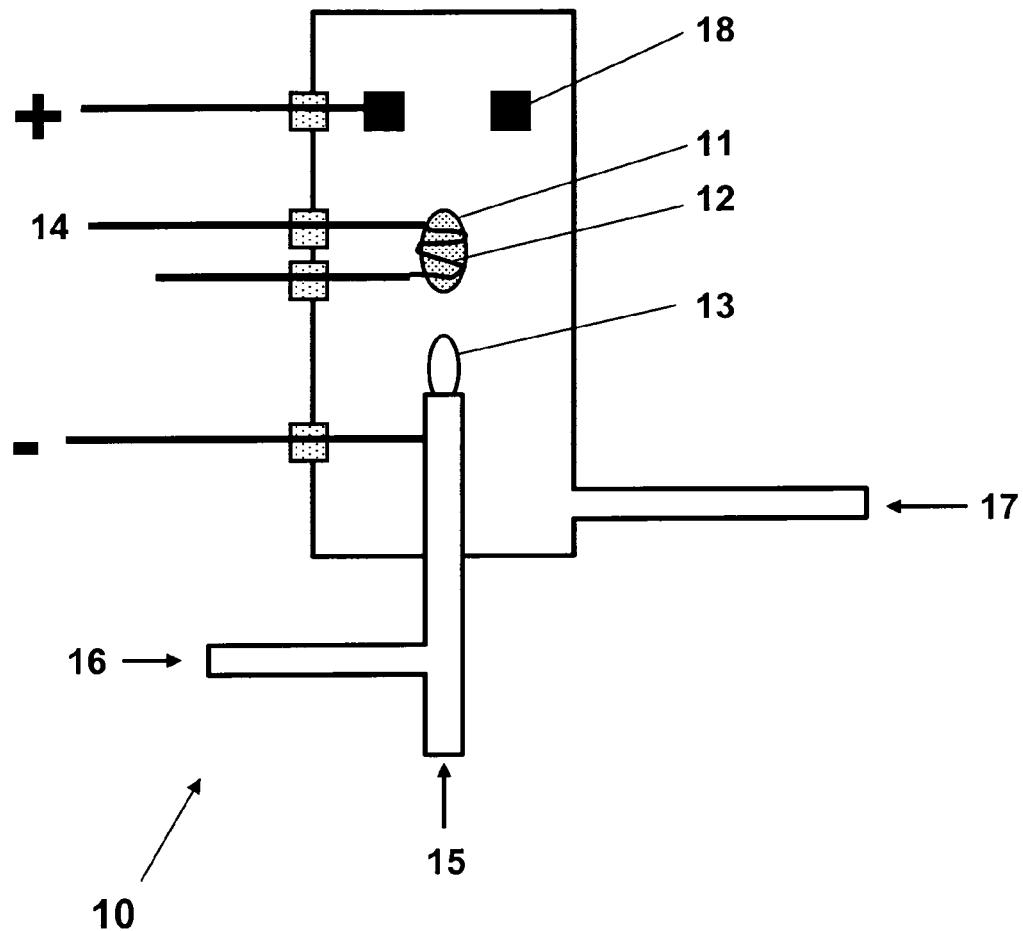
FIG. 1 shows a schematic illustration of a conventional thermionic detector.
Figure 2:
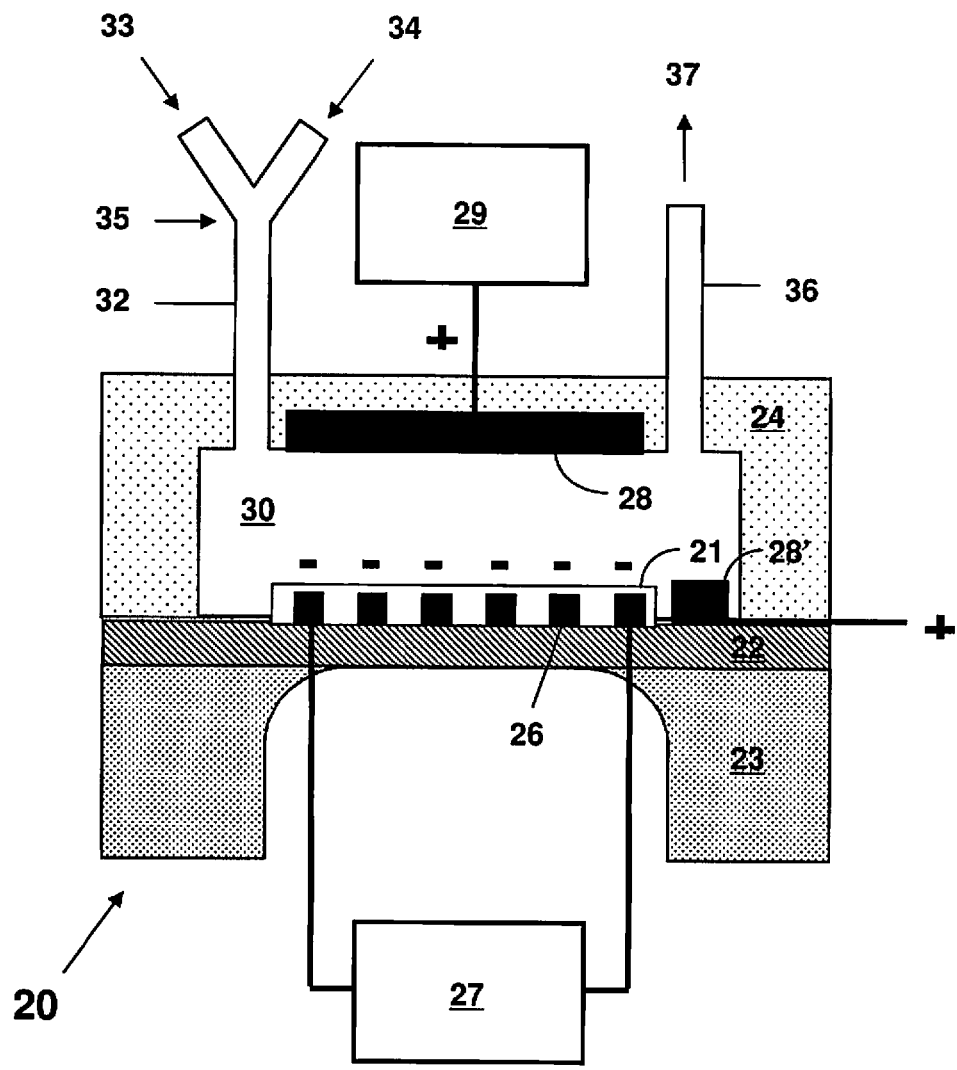
FIG. 2 shows a schematic illustration of a microfabricated thermionic detector.

In FIG. 2 is shown an exemplary microfabricated TID 20 of the present invention, wherein the microhotplate comprises a heated membrane 22 that is suspended from a substrate 23. The TID 20 can be microfabricated from semiconductor-based materials used in the microelectromechanical systems (MEMS) and integrated circuit (IC) industries. The microfabricated TID 20 comprises a low work function thermionic material deposited on the heated membrane 22 of the microhotplate. The low work function material thereby provides a heated thermionic source 21. A gas tight lid 24 attaches to the detection chamber side of the substrate 23 to seal the detection chamber 30. The detection chamber 30 can preferably have a diameter of a few millimeters and a height of about 0.15-1 mm. The lid 24 can have a gas inlet 32 for introduction of the sample and carrier gases into the detection chamber 30 and an exhaust gas outlet 36 for removal of the gaseous decomposition products 37. The gas inlet 32 can further comprise a pre-mixer section 35 for pre-mixing the sample and carrier gases 33 and 34. For example, the sample gas 33 can comprise a nitrogen- and/or phosphorous-containing compound. The carrier gas 34 can comprise hydrogen and/or make-up gas. Alternatively, the gases can be fed into the detection chamber 30 through separate gas inlets (not shown). Capillary tubes can be used as the gas inlet 32 and exhaust gas outlet 36. A resistive heating element 26 can be disposed on the detection chamber side (as shown) or on the opposite side of the membrane 22. The resistive heating element 26 can be resistively heated by electricity supplied by a power supply and control circuit 27. Electrical contact to the resistive heating element 26 can be established with perimeter bond pads (not shown). The perimeter bond pads and thin membrane 22 thermally and physically isolate the resistive heating element 26 and the detection chamber 30 from the electrical power source 27 and the substrate 23. The circuit 27 enables active temperature control of the thermionic source 21 by varying the power into the resistive heating element 26 to maintain a set resistance. The set point resistance, and therefore temperature, is user controlled. A feedback mechanism maintains constant heating element resistance, and hence constant thermionic source temperature. The microfabricated TID 20 has a high thermal sensitivity of typically better than 0.4 mW/° C. The microfabricated TID 20 can attain a temperature of 200° C. in less than 20 msec.

Thermal energy is provided by the heat from the electrically heated resistive heating element 26, not by combustion. Unlike the FID, there is no self-sustaining flame and the chemistry occurs only near the surface of the hot, thermionic source 21. As a result, nitrogen and phosphorous are ionized with high specificity by a surface-dominated process. The sensitivity of the microfabricated TID 20 depends on both the efficiency of the ion production as well as the efficiency of the ion collection. Therefore, the thermionic source 21 is preferably positioned so that the sample compounds impinge on the surface of the source and the resulting ionization is measured by an ion collector electrode 28 that is proximate the source 21. The efficiency of ion collection, in turn, depends on the magnitude and direction of the electric field produced within the detection chamber 30. Therefore, the placement of the electrode 28 will affect the response of the microfabricated TID 20. Therefore, the pattern of the electric field within the detector volume should be designed to maximize ion collection. Further, the collector electrode 28 should be well insulated electrically from neighboring structures to minimize leakage currents.

The ion collection electrode 28 can be positively biased relative to the thermionic source 21 to collect negatively charged ions emitted from the thermionic source when the source is heated by the microhotplate. The applied potential should be sufficiently large to accelerate the negative ions to the ion collection electrode, yet not so large as to result in arcing or ion multiplication. The electric field can be less than about 200 V/cm. Since the electrode spacing can be less than 0.1 cm, applied voltages of less than 20 V can be used. A sensitive electrometer 29 can be used to measure the ionization current generated by the thermionic source 21 and collected by the collection electrode 28.

Microfabrication of the Thermionic Detector

The microfabricated TID 20 can be formed by a fabrication method similar to that for the microcombustor. Unlike the microcombustor, that comprises a catalytic material for sustaining combustion, the microfabricated TID 20 of the present invention comprises a low work function material for the thermionic generation of negative ions. However, with the exception of the replacement of the combustion-sustaining catalytic material of the microcombustor with the low work function thermionic material, the processing steps of material deposition, photolithography, masking, etching, mask stripping and cleaning required to form the microfabricated TID 20 are similar to those disclosed by Gardner et al. and are generally well-known in the semiconductor IC industry.

The fabrication of the TID 20 comprises the steps of forming the suspended membrane 22 on the substrate 23, forming the resistive heating element 26 on the suspended membrane 22 to provide the microhotplate, and depositing the low work function thermionic material on the suspended membrane 22 to provide the thermionic source 21. The substrate 23 used to form the microfabricated TID 20 generally comprises a semiconductor (e.g., silicon or gallium arsenide) or a dielectric (e.g., a glass, quartz, fused silica, a plastic, or a ceramic), with a thickness generally about 400-500 µm. The suspended membrane 22 is typically formed as a rectangle or polygon with lateral dimensions from about one to a few millimeters on a side (e.g., a square of 1-3 mm on a side), or alternatively as a circle or ellipse with a size from one to a few millimeters. The suspended membrane 22 is supported at its edges by attachment to the substrate 23. The membrane 22 can be sufficiently thick (generally about 0.4-1 µm total thickness) for robustness as required for handling and to support the resistive heating element 26 and the thermionic source 21. Additionally, the membrane 22 can be sufficiently robust to withstand any stress induced by a mismatch in thermal expansion coefficients of the membrane 22 and the supporting substrate 23 upon heating to a thermionic temperature of over several hundred ° C. Low-pressure chemically vapor deposited silicon nitride is a preferred membrane material due to its low stress, low thermal conductivity, low heat capacity, and compatibility with IC processing steps. The low thermal conductivity minimizes heat loss to the substrate 23 and the low heat capacity enables heating of the detection chamber 30 to elevated temperatures. Other materials such as polycrystalline silicon, silicon oxynitride, and silicon carbide can also be used to form the membrane 22.

A silicon nitride suspended membrane 22 can be fabricated on a silicon substrate 23 by through-wafer etching of a silicon wafer. Either Bosch etching or KOH etching can be used to release the membrane 22, with no discernable operational differences between the completed devices made by either method. In the case of Bosch etching, an etch stop layer, for example 0.5 µm thermally-grown oxide, can be used to prevent undesired etching of the low-stress silicon nitride membrane layer. Any residual oxide remaining after the Bosch etch can be stripped in buffered HF. For KOH etching, no additional etch stop layer is required.

Prior to silicon etching by either method, the thin-film resistive heating element 26 can be patterned on the membrane layer on the opposite side of the silicon wafer from the etch window. The resistive heating element 26 generally can comprise one or more circuitous metal traces formed from one or more layers of deposited metals including platinum, molybdenum, titanium, chromium, palladium, gold, and tungsten that can be patterned on the upper (i.e., detection chamber) side of the membrane 22. Alternatively, the resistive heating element 26 can be patterned on the underside of the membrane 22. To form a platinum resistive heating element 26, a 10-nm-thick adhesion layer of titanium or tantalum, or oxides of these materials, can be deposited on the silicon nitride membrane layer 22 through a patterned photoresist mask having a circuitous opening therethrough, followed by deposition of a 170-nm-thick layer of platinum. The resistive heating element 26 generally covers about 50% of the area of the suspended membrane 22 that forms the detection chamber 30. The resistive heating element 26 can double as a temperature sensor by monitoring the resistance change of the wire caused by thermal fluctuations.

The electronic work function of the thermionic source 21 is determined by the composition of the thermionic surface. The composition preferably provides a low work function surface to facilitate the emission of charged particles from the heated thermionic source. The low work function material can be an alkali- or alkaline-earth-containing glass or ceramic material. The alkali metal is preferably Cs or Rb. The alkaline-earth metal is preferably Sr. Alternatively, other low work function materials can also be used, such as TiN or $LaB_6$. Preferably, the thermionic material is thermally robust and will not corrode the underlying membrane 22 and resistive heating element 26. The thermionic source 21 is disposed on the surface of the heated membrane 22 that is exposed to the detection chamber 30. The thermionic source 21 should preferably be thick enough to provide sufficient thermionic activity, but thin enough to allow for adequate heat transfer between the microhotplate surface and the thermionic material surface in contact with the gases to be analyzed.

Reliable deposition of thermionic materials is highly desirable in order to achieve consistent microfabricated TID performance. Typically, the thermionic material can be spray coated on the surface of the microhotplate. Slurry deposition and chemical vapor deposition also can be used to deposit thermionic materials in the past. A micropen deposition technique can also be used. The micropen dispenses a controllable volume of paste per time, which enables control of thickness by varying print volume, paste concentration, and write speed.

Another simple technique to deposit the low work function material is via sol-gel processes. For example, alkali metal hydroxide catalyzed sol gels comprising silicate ions and alkali metal ions, including cesium and rubidium, can be used. For example, a sol gel precursor solution, comprising tetraethylorthosilicate, cesium hydroxide, ethanol, and excess water can be sprayed, drop coated, or spin coated onto the surface of the microhotplate. Suitable ratios of alkali metal to silicon oxide are about 1 to 30% by weight.

The ion collection electrode 28 can be embedded in the detection chamber side in the lid 24, as shown. The lid 24 is preferably fabricated of a high-temperature dielectric material, such as Pyrex or ceramic. Alternatively, an electrode 28' can be patterned on the same substrate as the heater. Alternatively, the collection electrode 28 can be microfabricated in a micromachined channel placed over the thermionic source 21 or in the exhaust gas outlet 37. The measured ionization current can be quite small. Therefore, the electrode 28 should be sufficiently large to collect substantially all of the ionization current generated by the thermionic source 21. The collection electrode 28 can be of a stable, conducting material, such as a metal or a doped semiconductor. For example, the electrode 28 can be a small planar nickel electrode, of approximately 2 mm diameter.

Operation of the Microfabricated Thermionic Detector

In operation, the sample and carrier gases are flowed over the hot thermionic source. The sample compounds interact directly with the thermionic surface, which is heated by the resistive heating element. The electronegative products of the decomposition are selectively ionized by surface ionization on the thermionic source. The ionized decomposition products are then collected by the positively biased ion collection electrode, which can be kept at a potential of less than one hundred volts relative to the thermionic source.

The operating parameters are the electronic work function of the thermionic source material, the temperature of the thermionic source, and the chemical composition of the gas mixture surrounding the source. The thermionic surface temperature must be hot enough to form the electronegative decomposition products that are selectively ionized at the thermionic surface. Further, the specific response to the different compounds is highest when the thermionic surface temperature is relatively low. As the surface temperature is increased, the microfabricated TID responds to a wider variety of compounds. The operating temperature of the thermionic source is typically in excess 400° C., depending on the work function of the particular thermionic material used. The temperature of the thermionic source is affected by the current to the resistive heating element and heat losses to the surrounding microfabricated TID structure and to the gas flowing over the thermionic source. In particular, heat loss to the gas is related to the thermal conductivity of the gas mixture and the gas flow rate over the thermionic source. Typical gas flow in the microfabricated TID is as low as 2 milliliters per minute of air. The microfabricated TID can operate with or without hydrogen and, because of the small size of the device, makeup gas is not normally required.

The detection will also be very sensitive to the detailed electronegative character of the sample compound's molecular structure. Therefore, the compound-to-compound response of the microfabricated TID can vary widely. Further, the composition of the gas environment can be varied to suppress the response to certain compounds while enhancing the response to others. For example, the sensitivity and selectivity of the microfabricated TID for nitrogen and phosphorous can be strongly dependent on hydrogen flow rate. Further, when the thermionic source is operated in an oxygen-containing gas environment, rather than hydrogen, the response to halogenated compounds will be enhanced relative to nitrogen-containing compounds. The presence of the electronegative oxygen molecule changes the transfer of negative charge in a manner that enhances the specific ionization of halogenated compounds.

Figure 3:
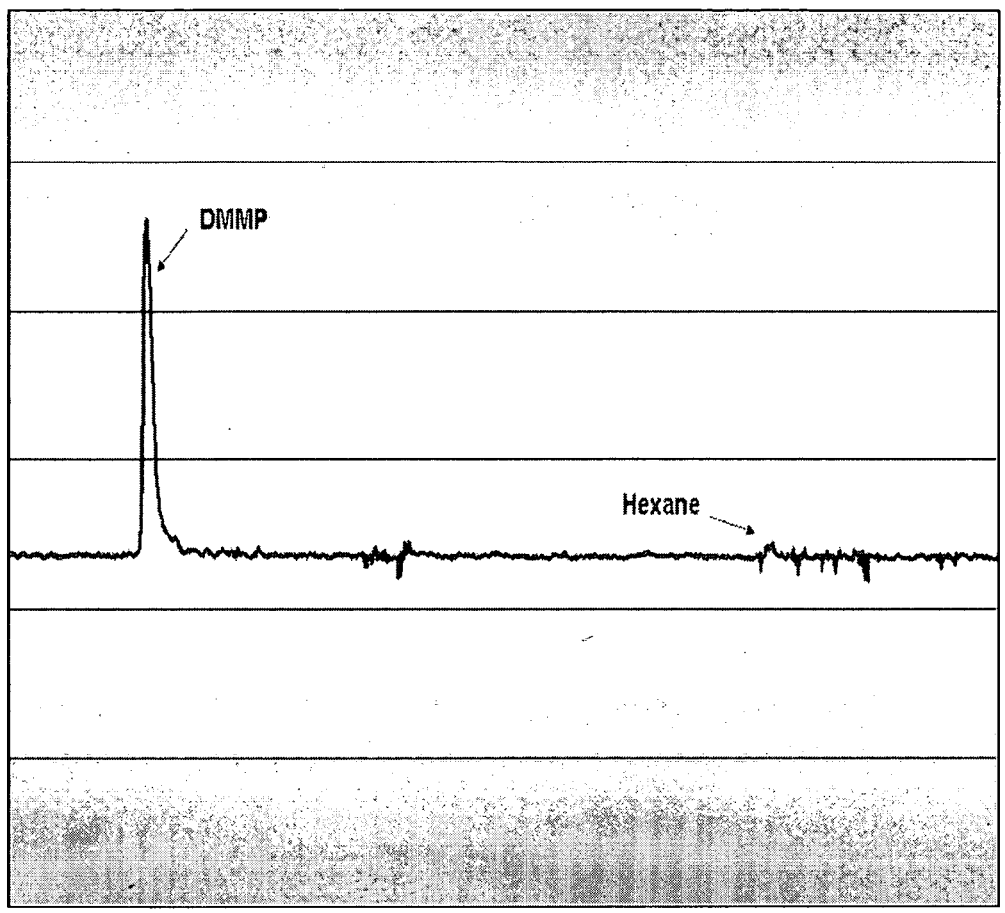
FIG. 3 shows the response of the microfabricated thermionic detector to dimethyl methyl phosphonate (DMMP) and hexane.

In FIG. 3 is shown the response of a microfabricated TID to a phosphorous-containing compound, dimethyl methyl phosphonate (DMMP), and a normal alkane, hexane. The thermionic material comprised a cesium hydroxide catalyzed sol gel. The composition of the sol gel was 2.31 grams CsOH monohydrate dissolved in 5 mL of 18 mΩ de-ionized water with the addition of 1 mL tetraethylorthosilicate. The resulting biphasic mixture was stirred at 1200 rpm on a 50° C. hotplate until a single phase was obtained. The sol gel mixture was spray coated on the membrane of the microfabricated TID. The membrane was heated to 600° C. using 370 mW of power. Two separate injections were made into the microfabricated TID. The first was a headspace injection of DMMP what has a vapor pressure of approximately 1 mmHg at 25° C. The second injection was hexane that has a vapor pressure of 151 mmHg at 25° C. The collected ionization current was measured with a commercial bias circuit and electrometer. As expected with the selective detector, there is a large difference in the response of the DMMP and the hexane. Selectivity was approximately 90,000:1 moles of phosphorous to mole of carbon. The microfabricated TID was also sensitive to nitrogen and did not require the use of hydrogen to detect nitro-functionalized compounds.

The present invention has been described as microfabricated thermionic detector. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A microfabricated thermionic detector, comprising:
   a microhotplate comprising
      a substrate having a suspended membrane formed thereon,
      a resistive heating element disposed on a surface of the suspended membrane, and
      a low work function material disposed on a surface of the suspended membrane exposed to a detection chamber to provide a thermionic source that generates negative ions from a sample gas comprising an electronegative function group;
   at least one gas inlet attached to the detection chamber for introduction of the sample gas thereinto;
   an exhaust gas outlet attached to the detection chamber for removal of decomposition products therefrom; and
   an ion collection electrode disposed in the detection chamber proximate the thermionic source, wherein the electrode is positively biased relative to the thermionic source and collects the negative ions generated by the sample gas reacting with the thermionic source when the suspended membrane is heated by the resistive heating element and a voltage is applied between the thermionic source and the electrode.

2. The microfabricated thermionic detector of claim 1, wherein the microhotplate is fabricated from materials selected from the group consisting of semiconductors and dielectrics.

3. The microfabricated thermionic detector of claim 2, wherein the materials comprise silicon-based materials.

4. The microfabricated thermionic detector of claim 3, wherein the silicon-based materials comprises materials selected from the group consisting of silicon nitride, polycrystalline silicon, silicon oxide, silicon oxynitride, and silicon carbide.

5. The microfabricated thermionic detector of claim 1, wherein the resistive heating element comprises a metal selected from the group consisting of platinum, molybdenum, titanium, chromium, palladium, gold, tungsten, and combinations thereof.

6. The microfabricated thermionic detector of claim 1, wherein the detection chamber comprises a lid and wherein the ion collection electrode is disposed on the lid.

7. The microfabricated thermionic detector of claim 1, wherein the ion collection electrode is disposed on the substrate.

8. The microfabricated thermionic detector of claim 1, wherein the low work function material comprises an alkali-containing material.

9. The microfabricated thermionic detector of claim 8, wherein the alkali-containing material comprises cesium or rubidium.

10. The microfabricated thermionic detector of claim 1, wherein the low work function material comprises a sol gel.

11. The microfabricated thermionic detector of claim 1, wherein the low work function material comprises an alkaline-earth-containing material.

12. The microfabricated thermionic detector of claim 11, wherein the alkaline-earth-containing material comprises strontium.

13. The microfabricated thermionic detector of claim 1, wherein the low work function material comprises TiN or $LaB_6$.

14. The microfabricated thermionic detector of claim 1, wherein the sample gas comprises a nitrogen- or phosphorous-containing compound.

15. The microfabricated thermionic detector of claim 1, wherein the sample gas comprises a halogen-containing compound.

16. The microfabricated thermionic detector of claim 1, wherein the detection chamber has a cross-sectional dimension of less than three millimeters.

17. The microfabricated thermionic detector of claim 1, wherein the detection chamber has a height of less than one millimeter.

* * * * *